United States Patent
Tangrea et al.

(10) Patent No.: US 10,016,151 B2
(45) Date of Patent: Jul. 10, 2018

(54) APPARATUS FOR DETECTING CELLS IN CIRCULATING BLOODSTREAM

(71) Applicant: LifeBridge Health, Inc., Baltimore, MD (US)

(72) Inventors: Michael A. Tangrea, Severna Park, MD (US); Sean O'Hearn, Baltimore, MD (US); Mauro Moscucci, Baltimore, MD (US)

(73) Assignee: LIFEBRIDGE HEALTH, INC., Baltimore, MD (US)

( * ) Notice: Subject to any disclaimer, the term of this patent is extended or adjusted under 35 U.S.C. 154(b) by 51 days.

(21) Appl. No.: 15/410,947

(22) Filed: Jan. 20, 2017

(65) Prior Publication Data

US 2017/0202494 A1 Jul. 20, 2017

Related U.S. Application Data

(60) Provisional application No. 62/281,100, filed on Jan. 20, 2016.

(51) Int. Cl.
*A61B 5/145* (2006.01)
*A61B 5/00* (2006.01)
(Continued)

(52) U.S. Cl.
CPC ........ *A61B 5/14546* (2013.01); *A61B 5/0205* (2013.01); *A61B 5/1459* (2013.01);
(Continued)

(58) Field of Classification Search
CPC . A61B 5/14546; A61B 5/1459; A61B 5/1473; A61B 5/14532; A61B 5/14539;
(Continued)

(56) References Cited

U.S. PATENT DOCUMENTS

| 5,324,275 A | 6/1994 | Raad et al. |
| 6,122,536 A * | 9/2000 | Sun ............... A61B 5/14532 600/317 |

(Continued)

FOREIGN PATENT DOCUMENTS

WO  2015/056257  4/2015

OTHER PUBLICATIONS

International Search Report issued in corresponding Application No. PCT/US17/14236 dated Apr. 10, 2016.

(Continued)

*Primary Examiner* — Eric Winakur
(74) *Attorney, Agent, or Firm* — Whiteford, Taylor & Preston, LLP; Peter J. Davis (57) ABSTRACT

A device for the real-time in vivo detection of a number of conditions within the patient, including CTCs, circulating nucleic acids, other circulating elements, blood pressure, heart rate data, pulse oxygen concentration, serum electrolyte concentrations, blood glucose, and pH, the device having an implanted subcutaneous access port in the chest region and a catheter having a terminus in the superior vena cava, the device having microelectronic circuitry with a rechargeable energy source encased in a titanium shell, an NIR laser sealed in the titanium-enclosed circuitry platform, and NIR-specific optical fibers (nir-FO) for transmitting the NIR photons to the end of the catheter tube in the superior vena cava. Scattered NIR photons are collected through the end of a second nir-FO bundle and transmitted back to the detector and microprocessor on the portal platform.

6 Claims, 5 Drawing Sheets

(51) Int. Cl.
*A61B 5/1455* (2006.01)
*A61B 5/0205* (2006.01)
*A61B 5/1459* (2006.01)
*A61B 5/1473* (2006.01)
A61B 5/0215 (2006.01)
A61B 5/024 (2006.01)

(52) U.S. Cl.
CPC ........ *A61B 5/1473* (2013.01); *A61B 5/14532* (2013.01); *A61B 5/14539* (2013.01); *A61B 5/14552* (2013.01); *A61B 5/6865* (2013.01); A61B 5/0215 (2013.01); A61B 5/02444 (2013.01)

(58) Field of Classification Search
CPC .............. A61B 5/14552; A61B 5/1455; A61B 5/14551; A61B 5/0205; A61B 5/6865; A61B 5/0215
See application file for complete search history.

(56) References Cited

U.S. PATENT DOCUMENTS

| | | | |
|---|---|---|---|
| 6,438,397 B1 * | 8/2002 | Bosquet | A61B 5/14532 600/310 |
| 7,809,441 B2 * | 10/2010 | Kane | A61B 5/14546 600/322 |
| 8,073,517 B1 | 12/2011 | Burchman | |

* cited by examiner

APPARATUS FOR DETECTING CELLS IN CIRCULATING BLOODSTREAM

FIELD OF THE INVENTION

This invention relates generally to in vivo detection of biological constituents in the bloodstream of a living mammal, and more particularly to a method and device for real time in vivo detection of circulating tumor cells in a patient's body.

BACKGROUND OF THE INVENTION

Cancer continues to claim the lives of hundreds of thousands of people in the United States every year. While advances have been made throughout the years in cancer detection and treatment, real-time detection of cancer recurrence and response to treatment in a person's body remains a challenge. Standard monitoring methods include magnetic resonance imaging (MRI) and other techniques, which evaluate disease progression at 3-month intervals. This approach is both expensive and may miss disease progression due to the time interval.

One potential advancement for monitoring disease progression is the detection of circulating tumor cells (CTCs), which are shed by active tumors in the body. The detection of CTCs could provide a novel method to track disease progression and response to treatment.

Currently, CTCs are detected from a patient blood sample. However, because there are very few CTCs, it is difficult to detect and quantify these entities from a blood draw using in vitro devices. The main disadvantage of this approach is sampling error. Typically only 7-10 cc of blood is drawn with scant, if any, CTCs in the sample, resulting in a significant sensitivity limitation.

Another detection approach requires insertion of a needle into the arm of a patient for a specified time period. The needle is then removed, and the CTCs are eluted off the tip of the device. While this method offers a tool for detecting CTCs, it does not record real-time data over the time course of treatment and is prone to sampling errors.

Accordingly, there remains a need for improved methods and devices for in vivo detection of CTCs, preferably in real-time and over the entire course of a patient's cancer treatment.

SUMMARY OF THE INVENTION

The present invention may be used to detect in vivo, in real time, a number of elements and conditions within the circulating bloodstream of a patient, including CTCs, circulating nucleic acids and proteins, immune response (via detecting changes to the white blood cell population), blood pressure, heart rate data, pulse oxygen concentration, serum electrolyte concentrations, blood glucose, and pH to provide comprehensive data related to the patient's health.

More specifically, the present invention is an advanced device that can detect circulating tumor cells in real-time. The additional information about CTCs gained from this invention will allow clinicians to properly adjust treatment to fit disease progression and improve patient outcomes.

The present invention is a system and method for in vivo CTC detection using a port-a-cath-type device equipped with an on-board/self-contained CTC detector and counter. The port-a-cath is an implantable venous access device used to draw blood and give treatments, including intravenous fluids, drugs, or blood transfusions. The port is placed under the skin (subcutaneous port), usually in the chest. It is attached to a catheter (a thin, flexible tube) that is guided (threaded) into a large vein above the right side of the heart called the superior vena cava. A port-a-cath may stay in place for many weeks or months. A needle is inserted through the skin into the port to draw blood or give fluids.

The port-a-cath format provides easy access to the patient's blood stream for drug delivery as well as blood draws without the need to continually "stick" the patient's arm each visit. Despite the added convenience and comfort for the patient, however, port-a-caths do not perform any additional functions between chemotherapy courses.

According to the present invention, however, an implantable venous access device is provided that may advantageously be used to detect CTCs in real-time and record the amount detected to track disease progression and response to treatment.

More particularly, implantable venous access devices configured in accordance with certain embodiments of the invention will detect and count the CTCs as they interact with the device but not actually capture the CTCs, because capturing CTCs could potentially result in an increased risk of embolism.

In order to effect such detection, the implantable venous access device in accordance with certain embodiments of the invention uses fiber optics (FO) for passive and/or active detection of CTCs. Importantly, FO sensors are immune to electromagnetic interference and suitable for use in highly charged magnetic fields, such as those generated by MRIs, which are used to assess disease status throughout the body.

Because of its placement in the vena cava, the implantable venous access device according to the invention is ideally positioned to survey cells within the patient's blood. The device of the invention may be used to detect CTCs throughout the course of treatment with self-contained microcircuitry within the implantable venous access device of the invention. CTCs will be identified within the in vivo blood stream by cell size and density through the use of near infrared (NIR) energy. To accomplish this, the circuitry is designed around a microprocessor to control a NIR diode laser and an amplified detector driven by an externally rechargeable, self-contained battery pack.

According to a preferred embodiment, the present invention uses NIR-optimized fiber optics (nir-FOs) to deliver light energy down the body of the catheter and return the collected scatter back to the detector. Higher efficacy is produced from using the smaller diameter, cladded fiber optic bundles to emit NIR energy and larger diameter cladded fiber optic bundles to collect and transmit the scattered photons back to the detector.

Additional modalities, such as ultrasound, nanowires, silicon based microelectrodes, fiber optic sensors and circuitry may be used for monitoring and recording these additional health parameters. For example, FO strands with alternative cladding, shape, material, and utilizing evanescent field interference can be designed specifically as pressure sensors, chemical sensors, fiber optic bio-sensors and DNA oligomers detector.

The invention summarized above may be better understood by referring to the following description, claims, and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

DETAILED DESCRIPTION OF THE INVENTION

The present invention provides a device for the real-time in vivo detection of a number of conditions within the patient, including CTCs, circulating nucleic acids and proteins, immune response, blood pressure, heart rate data, pulse oxygen concentration, serum electrolyte concentrations, blood glucose, and pH to provide comprehensive data related to the patient's health. While the examples herein are directed to the detection of CTCs, they are not intended to be limiting, as the invention may be used for the in vivo real time detection of any number of health related conditions that may be ascertained from a self-powered, micro-electronic circuitry functionalized porta-cath unit.

This device consists of an implanted subcutaneous access port in the chest region with the catheter terminus in the superior vena cava near the right atrium. The device remains in place during the course of the treatment, typically for months to several years.

By detecting and monitoring the incidence of CTCs in the patient's blood stream, it will be possible to accurately track disease progression in real-time via the catheter located in the superior vena cava. In vivo CTCs will be identified by cell size and density using near infrared (NIR) energy.

Figure 1:
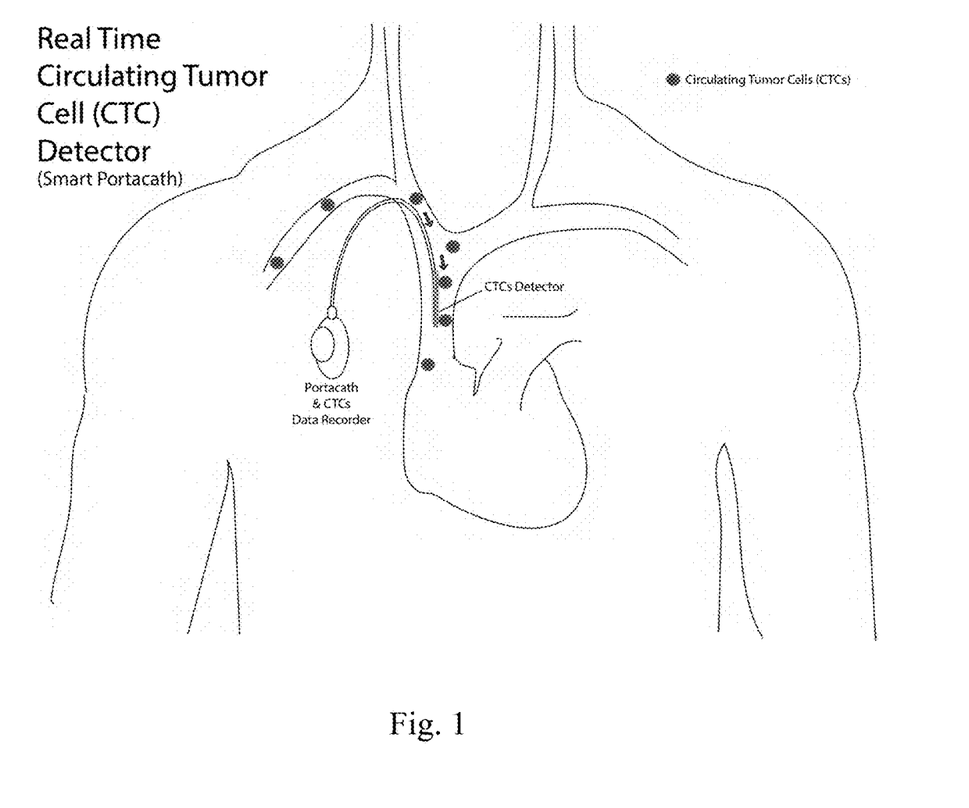
FIG. 1 is a representation of an embodiment of the invention implanted in a patient's vena cava and detecting CTCs in the patient's bloodstream.

FIG. 1 provides a schematic view of a CTC detecting device according to the invention configured in accordance with the foregoing aspects of the invention. As shown in FIG. 1, the device is positioned within the patient in traditional form and is configured to deliver treatment agents, such as chemotherapy, directly to the patient's blood stream. The distal end of the device includes a detector, as further described below, and the detector is configured to detect CTC's in the patient's bloodstream in real-time throughout the course of the patient's treatment. The proximal end of the device provides a digital memory arrangement for recording data over time corresponding to the amount of CTC's detected in the patient's bloodstream.

According to an embodiment of the invention, there is presented an implantable venous access system including microelectronic circuitry with a rechargeable energy source encased entirely within in a non-bioreactive titanium shell, similar to an automatic implantable cardiovertor-defibrillator (AICD).

The catheter portion of the device is looped through the right jugular vein and routed to the superior vena cava. The NIR laser is sealed in the titanium-enclosed circuitry platform. NIR-specific (low OH content or rare earth metal cladding) optical fibers (nir-FO) transmits the NIR photons to the end of the catheter tube in the superior vena cava. Scattered NIR photons are collected through the end of a second nir-FO bundle and transmitted back to the detector and microprocessor on the portal platform.

According to one embodiment of the invention, the device is fabricated to conform with existing porta-cath design parameters and modified as described below.

According to an embodiment of the invention, the device may include a catheter with sets of grooved channels longitudinal to the inside of the tubing. Multiple sets of nir-FOs may be glued into the grooves using medical grade silicon with the open termini set to the end of the catheter. The opposite ends of these fibers are pushed through designed openings on the circuit board and threaded into the NIR emitter and detector.

According to one embodiment of the invention, a collimator may be added to the FO end of the diode laser to help prevent dispersion of the energy. The FO may be optionally cladded to increase sensitivity by keeping the waveforms tight within the core of the FOs for both emission and detection. According to a further embodiment of the invention, bundles of cladded nir-FO may be used to transmit the most energy from the diode to the detector. According to a further embodiment, a smaller bundle is used to concentrate the emitted energy onto the cells and a larger bundle is used to collect the weaker scatter.

The circuitry to drive the NIR is located on a circular, donut-shaped printed circuit board with a hole in the center to accommodate the septum injection site of the portal. The circuitry board fits over the hole for the septum and rests on the portal platform. The microprocessor and memory is powered by an internal, self-contained direct current battery in the range of 7.2 V, 3000 mAh rechargeable metal ion battery. All components of the circuitry are protected by voltage regulators.

Additional solid state memory may be added to the circuitry for large data collection based on sampling frequency. For example, the invention may be used to measure clinically informative metrics such as CTCs per unit volume before and after the delivery of chemotherapy, as well as CTC count fluctuations over the course of treatment.

Collected data may be transmitted from the microprocessor memory via radio frequency (RF) technology similar to which has been adopted in AICD management. The data acquisition (DAQ) device supports several other solutions for data transmission, including serial-supported paired transceivers shields which operate in the unlicensed Industry, Science, and Medicine (ISM) band which are capable of transmitting at up to 100 mW and up to 300 kbps on personal area networks; in addition, simple WiFi can be used to connect to a wireless local area network operating within the Institute of Electrical and Electronic Engineers' standards (IEEE) 802.11 at 2.4 GHz connection, or some Bluetooth modules (OSEPP-type; class 1, 2.1+EDR supported). All are low powered (1.2-5 V, 50 mA), support file transfer protocols, and have encryption capabilities.

According to an embodiment of the invention, the optical fiber bundles used for the device may be assembled with fibers having single fiber diameters from 0.25 mm to 1.0 mm.

Efficacy is improved by using the smaller diameter, cladded FO bundles to emit NIR photons and larger diameter cladded FO bundles to collect and transmit the scattered photons back to the detector.

According to a preferred embodiment of the invention, there is presented a NIR-based platform (650 nm-1350 nm) directly detecting in vivo CTCs and other conditions and characteristics and anomalies that exist in a circulating bloodstream, by implementing similar principles of the forward and side scattering used in flow cytometry. The NIR photons are emitted from low powered (1 mW-400 mW) pulsed diode lasers. The energy at this power level is not ablative and is not adequate to produce a thermal effect in the tissue. Using flow cytometry, the forward scattering of light energy is used to measure volume. The readout of side scattering reveals the morphological complexity, granularity and density of cells, even those that are non-fluorescent. According to preferred embodiments of the invention, scatter is detected from angles of 80-175 degrees. As with flow cytometry, the arbitrary setting of threshold limits (gating) may be used to detect subpopulations of cells. In hematological flow applications the resolution can be digitally modulated to resolve granulocytes from monocytes from lymphocytes.

Figure 2:
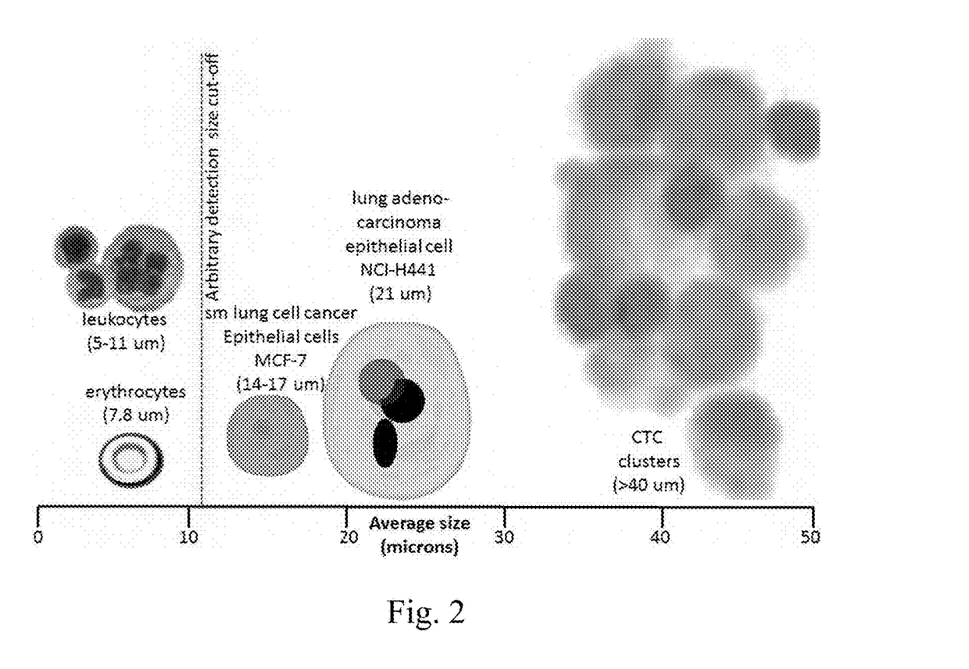
FIG. 2 is a graph showing blood cell and cancer cell and CTC cluster sizes together with a detection threshold.

Erythrocytes are biconcave, anucleated cells, averaging 7.7 microns in size. Leukocytes, including peripheral blood mononuclear cells (PBMCs), are nucleated and average 7-11 microns in size. In contrast, epithelial cells—possibly the origin of many CTCs—are typically 2-3 times the surface size of leukocytes starting at 14 microns in diameter. In addition, many CTCs are found as multicellular aggregates with irregular or elongated shapes >40 microns, and in multinucleated forms. The present invention is primarily (although not exclusively) focused on detecting cells greater than 12 microns in diameter. See FIG. 2.

According to an embodiment of the invention, a NIR optoelectronic emitter device is paired with a phototransistor detection unit with a visible light cut-off lens. The detection unit is coupled to a DAQ which includes an ATmega2560 microcontroller with an 8-bit AVR CPU and 256 kB flash memory operating at 16 MHz, but any commercially available DAQ may be used. A JAVA-based integrated development environment supports the processor commands as does modified C/C++ programming. The microprocessor can control emitter pulsed cycle duration of 32 milliseconds (mS) with a typical response time of 39 mS. These counts may be stored to the DAQ flash memory for future download and analysis.

The threshold size limit of the microprocessor may be programmed by varying the detected voltage amplitudes. These devices are rated at 5 volts (V) with the DAQ requiring 20-50 milliamps (mA) of current and the optoelectronic device requiring 30 mA.

According to a preferred embodiment, the light source is a 100 mW, 785 nm NIR diode laser with up to a 3 watt (W) output.

Sensitivity can be increased by coupling the diode laser to an indium gallium arsenide (InGaAs) 3V photodiode detector (3 mm2 active area; 750-1700 nm range) and focusing lens. The InGaAs photodiodes optoelectronic semiconductors are NIR-optimized for measuring both pulsed and continuous wavelength fiber light sources. Low voltage InGaAs transimpedence amplified photodetectors (TiAP) provide variable high gain control with low noise equivalent power and femtowatt ($10^{-15}$ watts) sensitivity, bypassing the possible need for a photomultiplier. Because the amplifier is attached to the detector, TiAP show higher signal-to-noise ratios compared to avalanche photodiodes. Moreover, TiAPs convert the output current into a voltage. The recorded voltage correlates to the magnitude of detected photon scatter with higher accuracy.

To limit the current through the diode and prevent overheating, a laser driver circuitry is provided to facilitate power conservation. According to a preferred embodiment, resistors set in parallel and a voltage regulator are used for the protective driver circuit.

Figure 3:
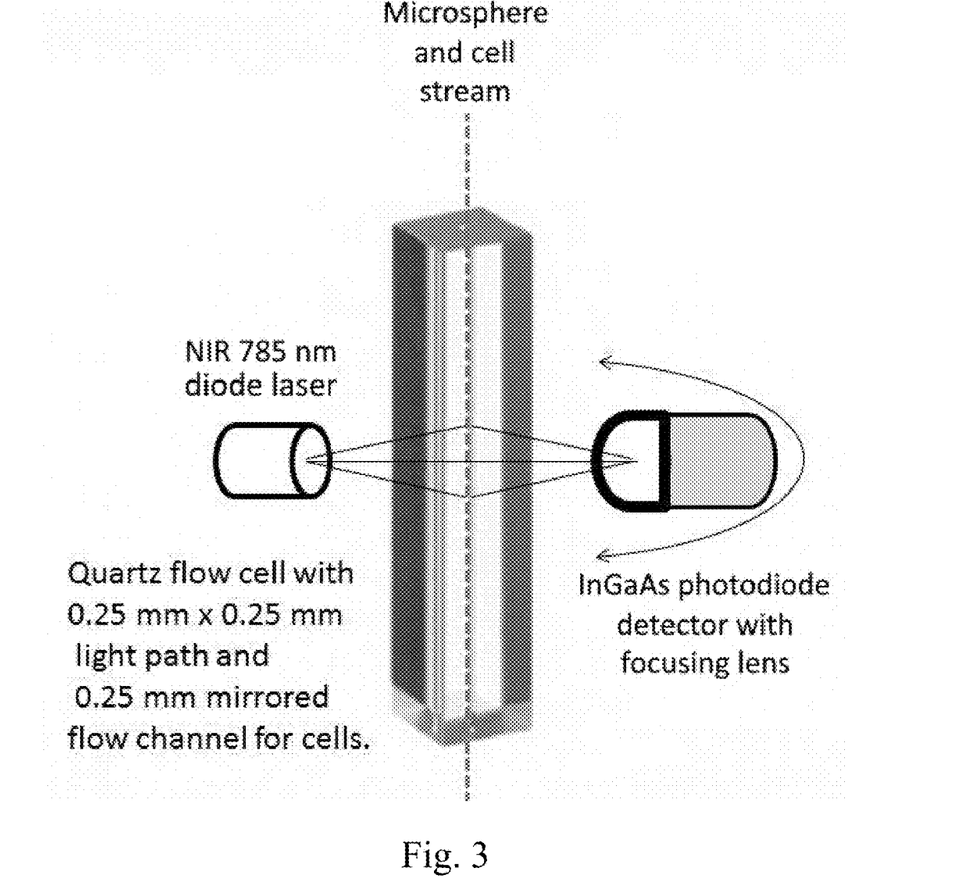
FIG. 3 is a representation of a quartz flow cell device coupled with a NIR 785 nm diode laser and InGaAs photodiode detector used for calibration of devices according to an embodiment of the invention.

For initial calibration (prior to implantation), the NIR laser is placed to the side of a quartz microfluidic flow cell (O.D. 4.2 mm) with a polished flow channel of 0.25 mm (I.D.). This particular quartz is rated at >84% NIR transmission. See FIG. 3. Aliphatic amine latex microspheres, ranging from sizes 0.02-15, flow through the channel in buffered saline solution, supplemented with AlexaFluor 649 as a masking agent (Light transmittance through suspensions of red blood cells show absorption above 600 nm). The microspheres flow perpendicular to the diode laser, exposing the cells to NIR energy. After collision with the cells, a portion of the scattered photons are collected by the InGaAs photodiode unit with the assist of an attached focusing lens. The NIR detector is in a planar rotation about the laser to optimize the angle of collecting scatter. Particular attention is given to any information contained in the backscattering produced by the beads. Beads greater than 1.5 microns produce detectable single particle scatter that increases with bead size. By adjusting the digital gain provided within the detecting unit and the DAQ programming, a cut-off size of 12 microns, or any arbitrary value, can be established. Baseline measurements are acquired from dyed saline (only) passing through the microfluidic channel. Calibration is performed from individual size microspheres in the buffer. Bead size determination, sensitivity, and percentage of sizes in the calibration standard can be verified by labeling the different beads with NIR-optimized fluorophores such as Dylight-830.

Direct labeling of the microspheres with NIR-sensitive fluorophores in the calibration step may be used to discern meaningful signals from noise.

Detecting CTC-mimetic cells with in vitro simulated blood flow.

Optical scattering occurs due to mismatches in refractive indices among different tissue components. Cell nuclei and mitochondria are the organelles that contribute most to scattering. Their dimensions range from 100 nm to 2 μm, and thus fall within the optimal NIR window of detection. These organelles exhibit highly anisotropic forward-directed scattering making them favorable for this application.

Precursors to CTCs could be cancerous epithelial cell lines such as MCF7, SKBr3, MD231, MD248, and T47D. These immortalized epithelial cells, typically >12 μm and cultured as adherent cells, can be enzymatically released from dishes both in the form of single cells and aggregates by modulating the timing of the chemical treatment. Size uniformity is controlled by passing the detached aggregates through a cellular sieve and verified with an optical microscope. These cells serve to mimic CTC in densities and morphologies. To test the device, individual epithelial cells, and their aggregates, are flowed through the channel. The sensitivity is evaluated by using labeled epithelial cells with specific fluorescent markers in NIR as a comparison.

Tests of the device according to the invention are carried out with simulated circulation using a Landorff-style heart perfusion stand with oxygenated Tyrode's solution as the artificial blood. The glassware, silicone tubing, and external pumps feed oxygenated, nutrient rich medium (Tyrode's) through a beating heart after it has been surgically extracted from an animal. An external pulsatile blood pump is used to replicate flow produced by the heart contractions. Importantly, the flow rates and pressures are accurately measured from sensors placed directly within the circulation flow on the stand. The glassware provides several 'ports' for the introduction of pharmacological agents and connections to other external devices. When the internal medium filters are removed from the system, live cells (and microspheres) can also be pumped through this artificial circulatory system and remain viable utilizing the same medium that keeps the heart alive.

The optical fibers of the device according to the invention are connected to the perfusion system through an available port. After recalibration using microspheres, the detection capacity is examined by measuring the density of CTC-mimetic epithelial cells injected into the circulating Tyrode's solution. The detection accuracy is examined by adding PBMCs, red blood cells, and purchased whole blood to the Tyrode's solution containing the CTC-mimetic epithelial cells. Counts from the device are compared against values obtained from flow cytometry. As expected, large nucleated cells containing an increased number of mitochondria, aggregates of these larger nucleated cells, and multinucleated cellular aggregates emit greater scattering signals than the enucleated red or smaller white blood cells.

Figure 4:
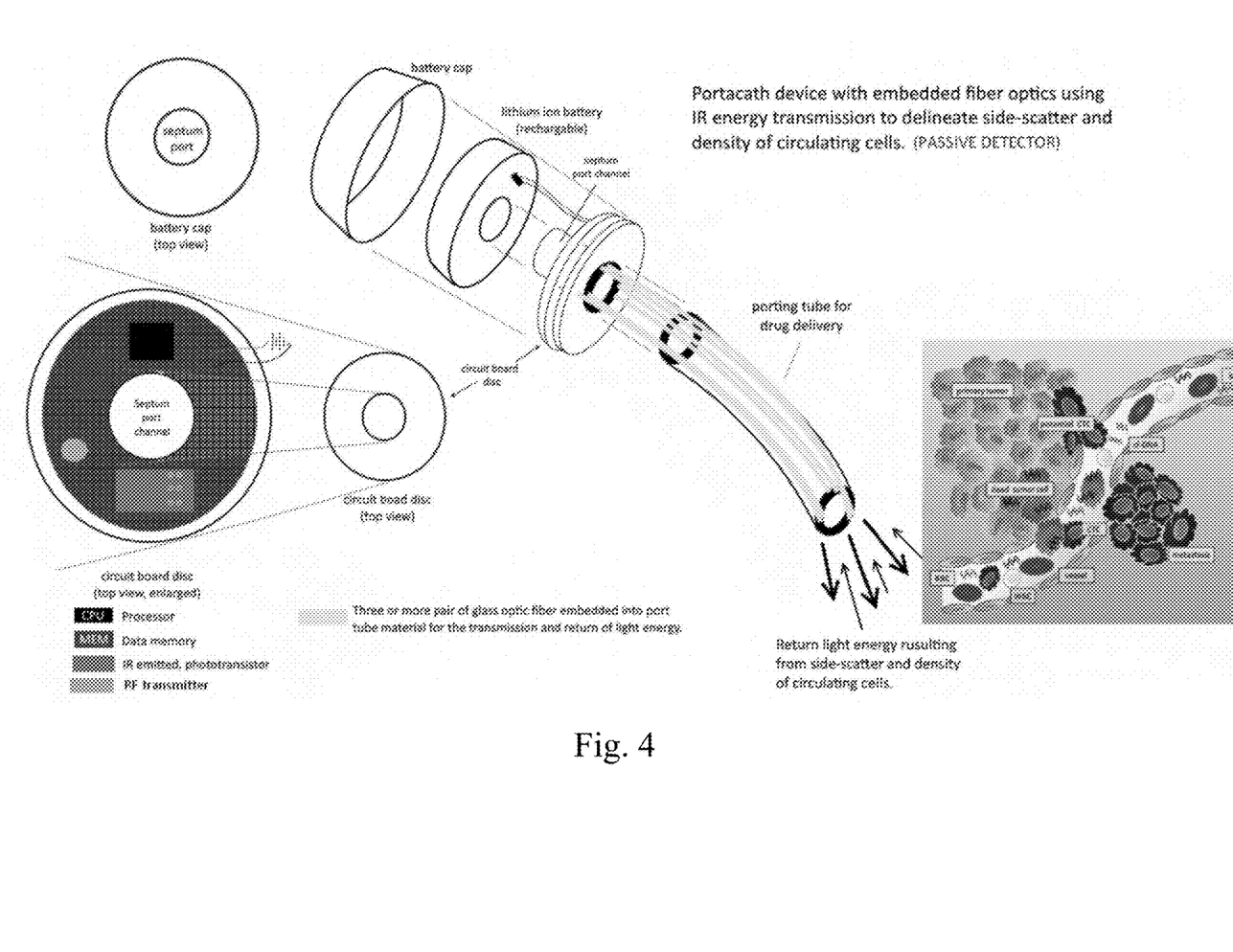
FIG. 4 is an exploded view of a passive detection device according to an embodiment of the invention.

FIG. 4 provides a detailed schematic view of a device according to an embodiment of the invention configured for use in a passive detection mode. In this configuration, the device has a port for implantation under the patient's skin and a catheter extending distally from the port. The port includes a battery cap, a battery (such as a rechargeable metal ion battery) positioned under the battery cap, and a port body having a septum for receiving a needle carrying the drug to be administered to the patient. The battery is of annular configuration such that the septum of the port body extends upward through the battery. The port body includes a circuit board carrying data collection, power and control electronics as further detailed below. In addition, the catheter includes preferably three or more pairs of glass optic fiber embedded into the tube material of the catheter, which transmit light between the port and the distal end of the catheter. In this configuration, the sensing head at the distal end of the catheter comprises the end of the optic fibers. The fibers project light onto cells in the patient's blood stream and receive light back that is dependent upon the side-scatter and density of the cells in the patient's blood stream. This configuration provides a passive detection scheme, in which the catheter with embedded fiber optics uses infrared energy transmission to delineate side-scatter and density of cells circulating in the patient's blood stream, allowing identification and quantitation in real time of CTCs in the patient's blood stream.

Figure 5:
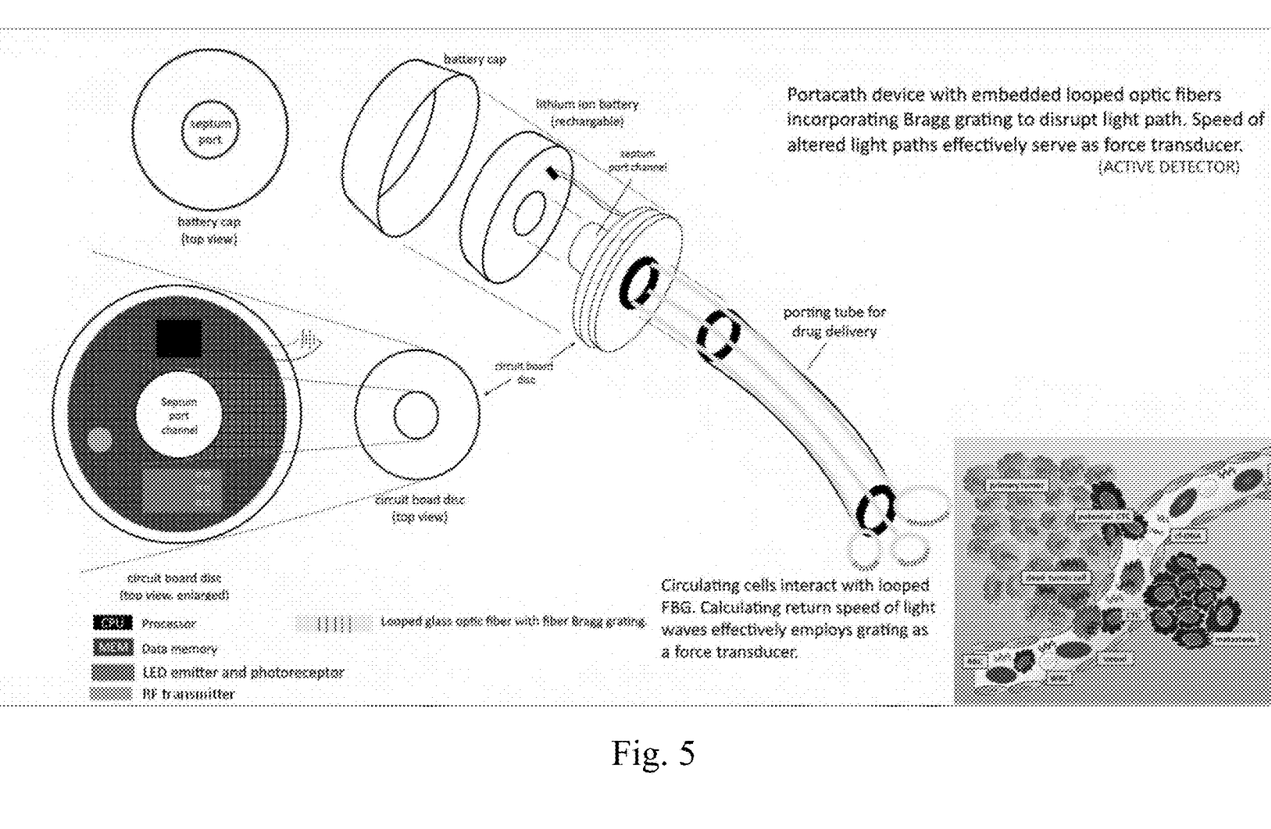
FIG. 5 is an exploded view of an active detection device according to a different embodiment of the invention.

FIG. 5 provides a detailed schematic view of the device according to the invention configured for use in an active interferometer detection mode. In this configuration, the device is provided having the same port configuration as that shown in FIG. 4 but which includes looped glass optic fiber with fiber Bragg grating (FBG). FBG is used to increase the sensitivity of the sensor system based on the interference principle. In this configuration, the sensing head at the distal end of the catheter comprises the looped FBG, such that cells circulating in the patient's blood stream interact with the looped FBG. The looped optic fibers incorporating FBG disrupt the light path projected into and returning through the optic fibers, such that the calculated speed of the altered light paths effectively serves as a force transducer to detect CTCs in the patient's blood stream.

With regard to the data collection, power and control electronics, the port is preferably configured to house the electronics for detection, such that the unit may be read wirelessly when the patient returns for chemotherapy. Alternatively, the unit may be read by a computer application resident on a smartphone or other portable computing device by the patient (see Figures). The electronics preferably include a CTC counter/processor, data memory, IR emitter/phototransistor (passive), LED emitter/photoreceptor (active) and RF transmitter, which elements are positioned on the circuit board in the port body.

In addition to CTCs, the device according to the invention may also be used to detect a number of other conditions within the patient, in vivo and in real time. Collected data from NIR absorption utilizing the nirFOs of the invention, may include hypoxemia and hypoxia conditions, blood pressure, heart rate data, and pulse oxygen concentration. Additional modalities, such as ultrasound, nanowires, fiber optic sensors, silicon based microelectrodes and circuitry may be used for monitoring and recording additional health parameters such as serum electrolyte concentrations such as potassium and sodium, blood glucose, blood pH, other electrolyte levels, and circulating nucleic acids and proteins. For example, fiber optic strands with alternative cladding, shape, material, and utilizing evanescent field interference can be designed specifically as pressure sensors, chemical sensors, fiber optic bio-sensors and DNA oligomers detector.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

The invention claimed is:

1. A device for monitoring conditions in the bloodstream of a living mammal, comprising:
   a port configured for implantation under a subject's skin, and
   a catheter extending distally from the port and having a sensing head at a distal end,
   the port comprising a battery cap, a battery compartment, and a port body having a septum for receiving a drug delivery needle;
   the battery having an annular configuration such that the septum of the port body extends upward through the battery;
   the port body including a circuit board carrying data collection, power and control electronics;
   the catheter having embedded therein a plurality of glass optic fiber pairs, the optic fiber pairs configured to transmit light between port and distal end of the catheter;
   the sensing head at the distal end of the catheter comprising the distal ends of the optic fibers,
   the optic fibers configured to project light onto cells in the subject's blood stream and receive light back that is dependent upon the side-scatter and density of the cells in the patient's blood stream.

2. A device according to claim 1, further comprising looped glass optic fiber pairs with fiber Bragg grating located at the sensing head at the distal end of the catheter configured to disrupt the light path projected into and returning through the optic fibers, such that the calculated speed of the altered light paths effectively serves as a force transducer to detect cell types in the patient's blood stream.

3. A device according to claim 2, further comprising an additional modality for monitoring and recording health-related parameters in the blood stream, said additional modality selected from one or more of the following: ultrasound, nanowires, fiber optic sensors, and silicon based microelectrodes and circuitry.

4. A device according to claim 2, further comprising an LED emitter/photoreceptor configured to direct photons into said optical fibers, and wherein said optical fibers comprise a first bundle of fibers for transmitting said light to a distal end of said optical fibers, said optical fibers also comprising a second bundle of optical fibers configured to collect scattered photons and transmit them to said circuit board.

5. A device according to claim 1, further comprising an additional modality for monitoring and recording health-related parameters in the blood stream, said additional modality selected from one or more of the following: ultrasound, nanowires, fiber optic sensors, and silicon based microelectrodes and circuitry.

6. A device according to claim 1, further comprising an NIR laser in the port body configured to direct NIR photons into said optical fibers, and wherein said optical fibers comprise a first bundle of NIR-specific optical fibers configured for transmitting said NIR photons to a distal end of said optical fibers, said optical fibers also comprising a second bundle of NIR-specific optical fibers configured to collect scattered NIR photons and transmit them to said circuit board.

* * * * *